US012616514B2

(12) United States Patent

Townley

(10) Patent No.: US 12,616,514 B2

(45) Date of Patent: May 5, 2026

(54) SYSTEMS AND METHODS FOR TREATING CHRONIC SINUSITIS

(71) Applicant: Neurent Medical Limited, Oranmore (IE)

(72) Inventor: David Townley, County Clare (IE)

(73) Assignee: Neurent Medical Limited, Oranmore (IE)

( * ) Notice: Subject to any disclaimer, the term of this patent is extended or adjusted under 35 U.S.C. 154(b) by 605 days.

(21) Appl. No.: 17/980,081

(22) Filed: Nov. 3, 2022

(65) Prior Publication Data

US 2023/0133359 A1     May 4, 2023

Related U.S. Application Data

(60) Provisional application No. 63/275,701, filed on Nov. 4, 2021.

(51) Int. Cl.
| | |
|---|---|
| *A61B 18/02* | (2006.01) |
| *A61B 18/14* | (2006.01) |
| *A61B 18/00* | (2006.01) |

(52) U.S. Cl.
CPC .......... *A61B 18/1485* (2013.01); *A61B 18/02* (2013.01); *A61B 2018/0022* (2013.01); *A61B 2018/00327* (2013.01); *A61B 2018/00434* (2013.01); *A61B 2018/00577* (2013.01); *A61B 2018/00642* (2013.01); *A61B 2018/1467* (2013.01)

(58) Field of Classification Search
CPC . A61B 18/1485; A61B 18/02; A61B 18/1815; A61B 18/20; A61B 18/082; A61B 2018/0022; A61B 2018/00327; A61B 2018/00434; A61B 2018/00577; A61B 2018/00642; A61B 2018/1467; A61B 2018/00267; A61B 2018/00708; A61B 2018/00791; A61B 2018/00839; A61B 2018/00875; A61N 7/022; A61N 2007/003

See application file for complete search history.

(56) References Cited

U.S. PATENT DOCUMENTS

| | | | |
|---|---|---|---|
| 874,178 | A | 12/1907 | De Forest |
| 3,117,571 | A | 1/1964 | Fry et al. |
| 3,538,919 | A | 11/1970 | Meyer |
| 3,941,121 | A | 3/1976 | Olinger et al. |
| 4,271,848 | A | 6/1981 | Turner et al. |
| 4,411,266 | A | 10/1983 | Cosman |

(Continued)

FOREIGN PATENT DOCUMENTS

| | | |
|---|---|---|
| WO | 2010/077980 A1 | 7/2010 |
| WO | 2016/183337 A2 | 11/2016 |

OTHER PUBLICATIONS

Arora, 1980, Cryodestruction of Vidian Nerve Branches, Indian Journal of Otolaryngology, 32(3):80-82.

(Continued)

*Primary Examiner* — Ankit D Tejani
*Assistant Examiner* — Joshua Brendon Solomon
(74) *Attorney, Agent, or Firm* — Brown Rudnick LLP; Adam M. Schoen

(57) ABSTRACT

The invention generally relates to systems and methods for targeting of specific tissue(s) of interest within a sino-nasal region of a patient, specifically sinus regions (i.e., ostia and sinus cavities), for the treatment of chronic sinusitis conditions.

13 Claims, 10 Drawing Sheets

(56)                  References Cited

U.S. PATENT DOCUMENTS

| | | | |
|---|---|---|---|
| 5,562,720 | A | 10/1996 | Stern et al. |
| 5,575,788 | A | 11/1996 | Baker et al. |
| 5,746,224 | A | 5/1998 | Edwards |
| 5,766,605 | A | 6/1998 | Sanders et al. |
| 5,800,429 | A | 9/1998 | Edwards |
| 6,033,397 | A | 3/2000 | Laufer et al. |
| 6,273,886 | B1 | 8/2001 | Edwards et al. |
| 6,517,534 | B1 | 2/2003 | McGovern et al. |
| 6,517,535 | B2 | 2/2003 | Edwards |
| 6,669,689 | B2 | 12/2003 | Lehmann et al. |
| 6,685,648 | B2 | 2/2004 | Flaherty et al. |
| 7,608,275 | B2 | 10/2009 | Deem et al. |
| 7,655,243 | B2 | 2/2010 | Deem et al. |
| 8,105,817 | B2 | 1/2012 | Deem et al. |
| 8,133,497 | B2 | 3/2012 | Deem et al. |
| 8,338,164 | B2 | 12/2012 | Deem et al. |
| 8,636,684 | B2 | 1/2014 | Deem et al. |
| 8,936,594 | B2 | 1/2015 | Wolf et al. |
| 8,939,970 | B2 | 1/2015 | Stone et al. |
| 8,961,391 | B2 | 2/2015 | Deem et al. |
| 9,072,597 | B2 | 7/2015 | Wolf et al. |
| 9,415,194 | B2 | 8/2016 | Wolf et al. |
| 9,498,283 | B2 | 11/2016 | Deem et al. |
| 9,700,707 | B2 | 7/2017 | Deem et al. |
| 10,022,529 | B2 | 7/2018 | Deem et al. |
| 10,052,465 | B2 | 8/2018 | Deem et al. |
| 10,307,200 | B2 | 6/2019 | Saadat |
| 10,610,675 | B2 | 4/2020 | Deem et al. |
| 10,729,897 | B2 | 8/2020 | Deem et al. |
| 10,894,011 | B2 | 1/2021 | Deem et al. |
| 11,033,318 | B2 | 6/2021 | Wolf et al. |
| 11,241,271 | B2 | 2/2022 | Wolf et al. |
| 11,679,077 | B2 | 6/2023 | Deem et al. |
| 11,766,286 | B2 | 9/2023 | Wolf et al. |
| 2005/0171574 | A1 | 8/2005 | Rubinsky et al. |
| 2005/0240147 | A1 | 10/2005 | Makower et al. |
| 2007/0219600 | A1 | 9/2007 | Gertner et al. |
| 2007/0287994 | A1 | 12/2007 | Patel |
| 2008/0021369 | A1 | 1/2008 | Deem et al. |
| 2014/0114233 | A1 | 4/2014 | Deem et al. |
| 2014/0243793 | A1 | 8/2014 | Morriss et al. |
| 2016/0331459 | A1 | 11/2016 | Townley et al. |
| 2018/0133460 | A1 | 5/2018 | Townley et al. |
| 2020/0179682 | A1 | 6/2020 | Townley et al. |
| 2020/0179683 | A1* | 6/2020 | Townley .............. G06T 7/0012 |
| 2020/0405383 | A1 | 12/2020 | Townley |

OTHER PUBLICATIONS

Chen, 2005, Radiofrequency treatment of nasal posterior-under nerve ethmoidal nerve and infraturbinal for perennial allergic rhinitis under nasal endoscope, China Journal of Endoscopy, 11(3):239-243.

Fang, 2005, Nasal endoscopy combined with multiple radiofrequency for perennial allergic rhinitis, J. First Mil. Medic Univ., 25(7):876-877.

Kong, 2005, Low-temperature plasma ablation of inferior turbinate for the treatment of perennial allergic rhinitis, 19:5 J Clin Otorhinolaryngol (China), 19:5:214.

Lane, 2004, Nasal anatomy and physiology, Facial Plast Surg Clin North Am., 12(4):387-395.

Liang, 1999, Radiofrequency treatment of ethmoidal nerve with allergic rhinitis under nasal endoscopy, J. Clin Otorhinolaryngol, 13(8):341-342.

* cited by examiner

Therapeutic System
100

Treatment Device
102

Console
104

Generator
106

Controller
107

Monitoring
System
108

Evaluation /
Feedback
Algorithms
110

Interface
112

114a

116

114b

116

114c

114d

Maxillary sinus ostium

Maxillary sinus cavity

Support element

Electrodes

Frame with Electrode Array

Maxillary sinus
ostium

Ostium implant

Cavity implant

SYSTEMS AND METHODS FOR TREATING CHRONIC SINUSITIS

CROSS-REFERENCE TO RELATED APPLICATIONS

This application claims priority to, and the benefit of, U.S. Provisional Application No. 63/275,701, filed Nov. 4, 2021, the content of which is incorporated by reference herein in its entirety.

FIELD OF THE INVENTION

The invention generally relates systems and methods for treating medical conditions, and, more particularly, to systems and methods for the treatment of a chronic sinusitis condition.

BACKGROUND

There are various conditions related to the sino-nasal cavity which may impact breathing and other functions of the nose. One of the more common conditions is rhinitis, which is defined as inflammation of the membranes lining the nose. The symptoms of rhinitis include sino-nasal blockage, obstruction, congestion, sino-nasal discharge (e.g., rhinorrhea and/or posterior sino-nasal drip), facial pain, facial pressure, and/or reduction or complete loss of smell and/or taste. Sinusitis is another common condition, which involves an inflammation or swelling of the tissue lining the sinuses, which can lead to subsequent. Rhinitis and sinusitis are frequently associated with one another, as sinusitis is often preceded by rhinitis. Accordingly, the term rhinosinusitis is often used to describe both conditions.

Depending on the duration and type of systems, rhinosinusitis can fall within different subtypes, including allergic rhinitis, non-allergic rhinitis, chronic rhinitis, acute rhinitis, recurrent rhinitis, chronic sinusitis, acute sinusitis, recurrent sinusitis, and medical resistant rhinitis and/or sinusitis, in addition to combinations of one or more of the preceding conditions.

Chronic sinusitis is one of the more prevalent chronic illnesses affecting persons of all age groups. It is an inflammatory process that involves the paranasal sinuses and persists for twelve weeks or longer. Chronic sinusitis is almost always accompanied by concurrent nasal airway inflammation and is often preceded by rhinitis symptoms. Accordingly, the term chronic rhinosinusitis is sometimes used.

Most cases of chronic sinusitis are continuations of unresolved acute sinusitis. However, chronic sinusitis usually manifests differently from acute sinusitis. Symptoms of chronic sinusitis include, but are not limited to, nasal stuffiness, postnasal drip, facial fullness, and general malaise. Chronic sinusitis can be brought on by an infection, growths in the sinuses (nasal polyps), and/or swelling of the lining the sinuses.

Current medical therapy for treating chronic sinusitis is generally focused on reestablishing sinus ventilation by opening sinus ostia. Such therapy includes pharmacotherapy (i.e., antibiotics, decongestants, nasal saline sprays, mast cell stabilizers, and expectorants) and/or surgical intervention (i.e., functional endoscopic sinus surgery (FESS)), which may further be followed by use of implants of one form or another (i.e., stents and or balloons). However, current therapy has its drawbacks. For example, pharmaceutical agents prescribed for chronic sinusitis generally need to be taken on a long-term basis, incurring costs and side effects (e.g., sedation, irritation, impairment to taste, sore throat, dry nose, etc.) and often have suboptimal efficacy. Surgical treatment has inherent risks and complications, ranging from bleeding and scarring to the use of general anesthetic, as well as increased recovery time and the potential to damage otherwise healthy tissue resulting in unintended side effects.

SUMMARY

The invention recognizes that a problem with current aids and surgical procedures for treating chronic sinusitis are either temporary or are not accurate and further fail to adequately treat the underlying cause, thereby failing to adequately address chronic sinusitis symptoms.

The invention solves these problems by providing systems and methods for treating chronic sinusitis by providing, among other things, therapeutic modulation of neural structures associated with chronic sinusitis conditions. For example, the present invention includes a treatment device including an end effector for delivering energy to target sites within the nasal cavity, which may include sinus ostia, sinus cavity walls, or a combination of both. The energy delivered to the target site(s) is sufficient to therapeutically treat tissues of interest associated with the sinuses, specifically neural tissue. In particular, energy delivered to the target site(s) may be sufficient to therapeutically modulate or interrupt neural signals associated with parasympathetic nerves that control autonomic function of the sinuses, thereby reducing or completely eliminating hyperactive mucosal secretions and soft tissue engorgement, thereby treating chronic sinusitis or related indications.

The treatment device may include various forms of an end effector shaped and/or sized to be positioned within a nasal cavity and relative to target sites associated with the sinuses, including, but not limited to, sinus cavities, including sinus cavity walls, and ostia of the sinuses, as well as a combination of both. For example, in some embodiments, the end effector may generally include one or more flexible support elements, each of which may include at least one energy delivering element for delivering treatment energy to the desired target site. The flexible support elements may include a specific geometry once deployed within the nasal cavity to complement anatomy of a respective location, such that a given support element may contact and generally conform to a shape of a respective location (i.e., sinus cavity wall, surface of a sinus ostium, etc.), at which point energy may be delivered to the underlying tissue (i.e., neural tissue) at a target site.

For example, the end effector may be comprised of a plurality of connected flexible support elements that, as a whole, form an expandable frame or basket able to transition from a retracted state (i.e., smaller radial profile) to a deployed state (i.e., expanded to a larger radial profile). In other embodiments, the end effector may include one or more flexible support elements having a helical- or coil-type shape once deployed. Yet still, on other embodiments, the end effector may include a dogbone- or dumbbell-type configuration, wherein a first set of flexible support elements forms a first segment and a second set of flexible support elements forms an opposing second segment. The end effector may also include one or more inflatable members (i.e., balloons or the like), either alone or incorporated with the flexible support element(s).

The energy delivering elements may include electrodes or the like configured to apply electromagnetic neuromodulation energy (e.g., radiofrequency (RF) energy) to target sites.

It should be noted that, in other embodiments, the end effector may include other energy delivery elements configured to provide therapeutic neuromodulation using various other modalities, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power.

Once the end effector is delivered within the sino-nasal cavity and positioned relative to the desired target site(s) (i.e., ostia and/or cavities of the sinuses), portions of the end effector (i.e., flexible support elements, outer surface of inflatable body, etc.) can transition to a deployed state, having a specific shape and/or size corresponding to anatomical structures within the sino-nasal cavity and associated with target sites to undergo delivery of therapeutic energy for treatment of chronic sinusitis. As such, once deployed, the energy delivery element(s) can be positioned at desired locations for focused application of energy to the underlying targeted neural tissue at the one or more target sites.

Accordingly, the systems and methods of the present invention allow for accurate, minimally invasive, and localized application of energy to one or more target sites within the sino-nasal cavity to disrupt neural signals associated with parasympathetic nerves that control autonomic function of the sinuses to thereby treat chronic sinusitis or related indications. By treating the underlying cause of chronic sinusitis, the present invention is able to better address the symptoms without the inherent risks and drawbacks associated with pharmacotherapy and surgical treatments.

DETAILED DESCRIPTION

There are various conditions related to the sino-nasal cavity which may impact breathing and other functions of the nose. One of the more common conditions is chronic sinusitis. It is a disease in which a natural orifice is closed due to the swelling of the mucous membrane by inflammation of paranasal sinuses and the storage of mucus in the sinus or generation of polypoid tissues (nasal polyps) in the nasal cavity occurs, thereby causing clinical symptoms such as nasal discharge, nasal obstruction, postnasal drip, and dull headache.

Figure 1:
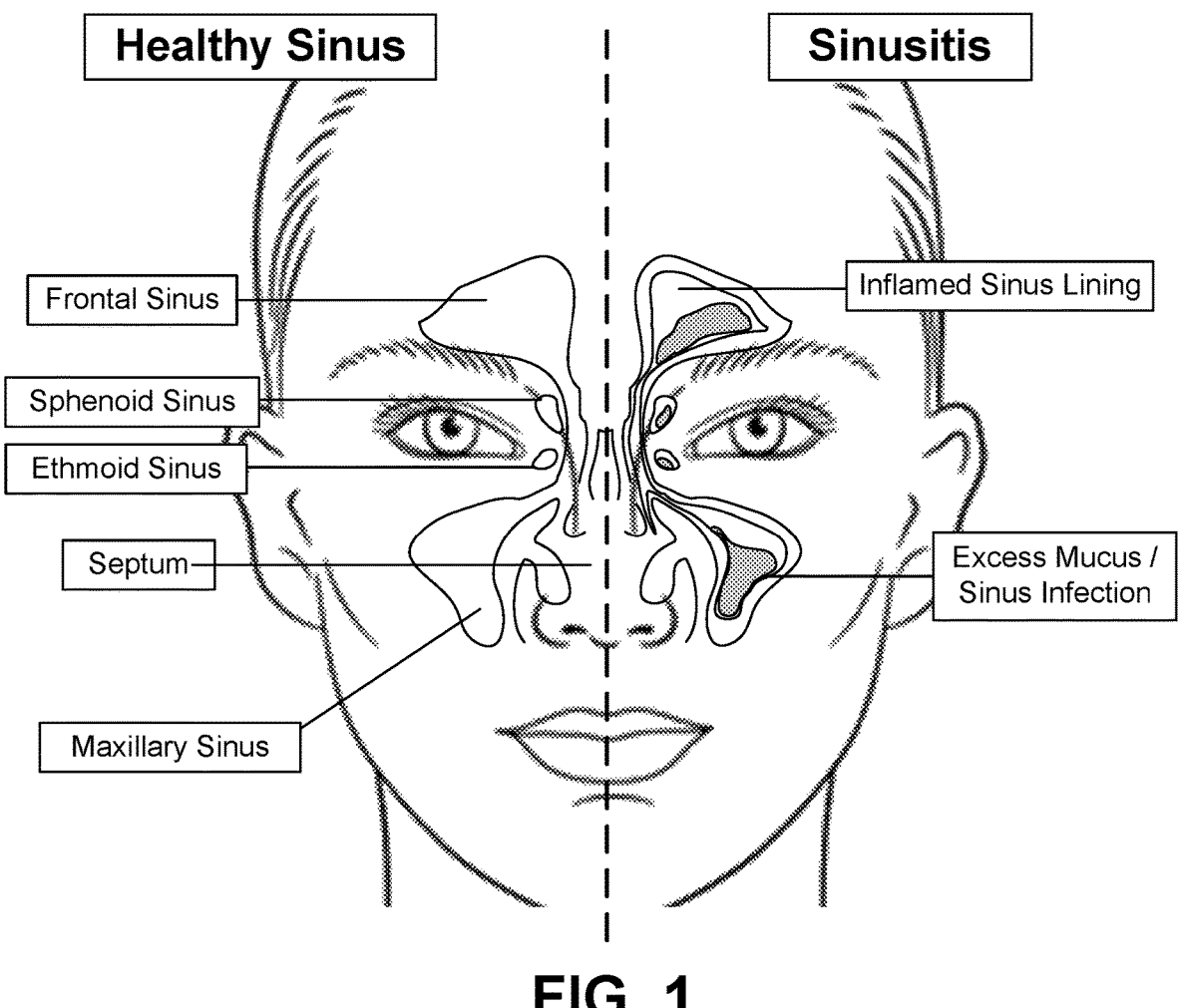
FIG. 1 is an image illustrating anatomy of paranasal sinuses, and further illustrating symptoms of chronic sinusitis.

FIG. 1 is an image illustrating anatomy of paranasal sinuses, and further illustrating symptoms of chronic sinusitis. The paranasal sinuses consist of air-filled spaces located within the bones of the skull and facial bones. They are centered on the nasal cavity and have various functions, including lightening the weight of the head, humidifying and heating inhaled air, increasing the resonance of speech, and serving as a crumple zone to protect vital structures in the event of facial trauma. Four sets of paired sinuses include: maxillary; frontal; sphenoid; and ethmoid. The pairs of paranasal sinuses are lined with ciliated, pseudostratified columnar epithelium. Goblet cells are interspersed among the columnar cells. The mucosa is attached directly to the bone. Involvement of the surrounding bone and further extension of the infection into the orbital and intracranial compartments can result from inadequate treatment of sinusitis and specific types of sinusitis.

The maxillary sinus is the largest paranasal sinus and lies inferior to the eyes in the maxillary bone. The frontal sinus is housed in the frontal bone superior to the eyes in the forehead. The sphenoid sinus originates in the sphenoid bone at the center of the head. The ethmoid sinuses arise in the ethmoid bone, forming several distinct air cells between the eyes.

The maxillary, frontal, and anterior ethmoid sinuses drain through their ostia located at the ostiomeatal complex lying lateral to the middle turbinate within the middle meatus. The posterior ethmoid and sphenoid sinuses open into the superior meatus and sphenoethmoid recess, respectively. The maxillary ostium is connected to the nasal cavity by a narrow tubular passage called the infundibulum, located at the highest part of the sinus; hence, drainage from the maxillary sinus flows against gravity via mucociliary clearance. Because the floor of the maxillary sinus is the tooth-bearing part of the maxilla, dental infections can easily extend to the maxillary sinus. Although the nasal cavity is usually colonized with bacteria, the sinuses are typically sterile.

Chronic sinusitis is caused by various factors, and it is considered that this disease is influenced by bacterial or viral infection, allergic reaction, genetic factors, living environment, etc. Stasis of secretions inside the sinuses can be triggered by (1) mechanical obstruction at the ostiomeatal complex due to anatomic factors or (2) mucosal edema caused by various etiologies (e.g., acute viral or allergic rhinitis).

Mucous stagnation in the sinus forms a rich medium for the growth of various pathogens. The early stage of sinusitis is often a viral infection that generally lasts up to 10 days and that completely resolves in a majority of cases. However, a small number of patients may develop a secondary acute bacterial infection that is generally caused by aerobic bacteria (i.e., *Streptococcus pneumoniae, Haemophilus influenzae, Moraxella catarrhalis*). Initially, the resulting acute sinusitis involves only one type of aerobic bacteria. With persistence of the infection, mixed flora, anaerobic organisms, and, occasionally, fungus contributes to the pathogenesis, with anaerobic bacteria of oral flora origin often eventually predominating. Most cases of chronic sinusitis are due to acute sinusitis that either is untreated or does not respond to treatment.

Many support the concept that chronic sinusitis is predominantly a multifactorial inflammatory disease. Confounding factors that may contribute to inflammation include the following: persistent infection (including biofilms and osteitis); allergies and other immunologic disorders; intrinsic factors of the upper airway; superantigens; and colonizing fungi that induce and sustain eosinophilic inflammation. All of these factors can play a role in disruption of the intrinsic mucociliary transport system. This is because an alteration in sinus ostia patency, ciliary function, or the quality of secretions leads to stagnation of secretions, decreased pH levels, and lowered oxygen tension within the sinus. These changes create a favorable environment for bacterial growth that, in turn, further contributes to increased mucosal inflammation.

The invention recognizes that a problem with current aids and surgical procedures for treating chronic sinusitis are either temporary or are not accurate and further fail to adequately treat the underlying cause, thereby failing to adequately address chronic sinusitis symptoms.

The invention solves these problems by providing systems and methods for treating chronic sinusitis by providing, among other things, therapeutic modulation of neural structures associated with chronic sinusitis conditions. For example, the present invention includes a treatment device including an end effector for delivering energy to target sites within the nasal cavity, which may include sinus ostia, sinus cavity walls, or a combination of both. The energy delivered to the target site(s) is sufficient to therapeutically treat tissues of interest associated with the sinuses, specifically neural tissue. In particular, energy delivered to the target site(s) may be sufficient to therapeutically modulate or interrupt neural signals associated with parasympathetic nerves that control autonomic function of the sinuses, thereby reducing or completely eliminating hyperactive mucosal secretions and soft tissue engorgement, thereby treating chronic sinusitis or related indications.

Figures 2A, 2B:
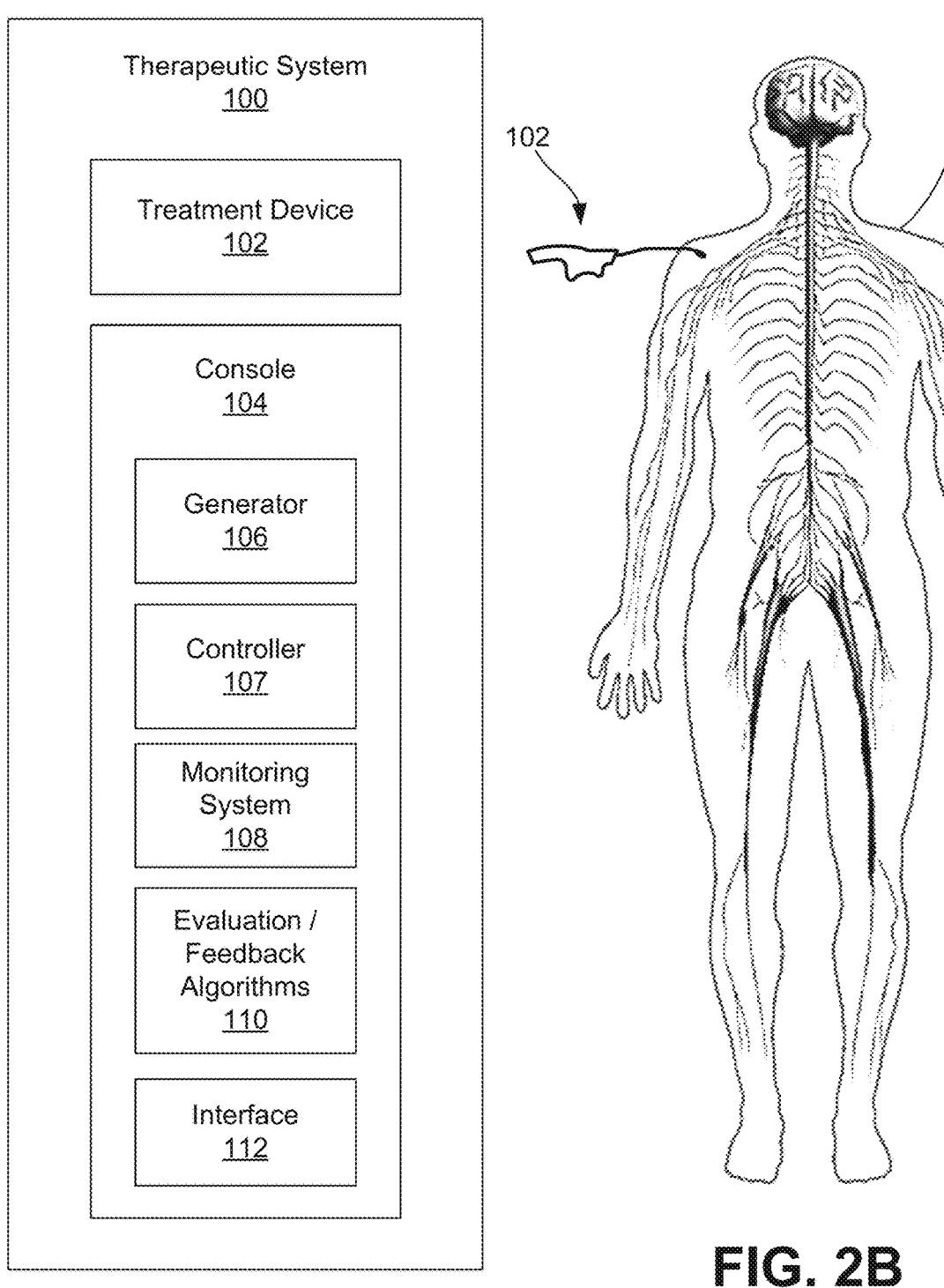
FIGS. 2A and 2B are diagrammatic illustrations of a system for treating chronic sinusitis conditions of a patient using a handheld device according to some embodiments of the present disclosure.
Figure 3:
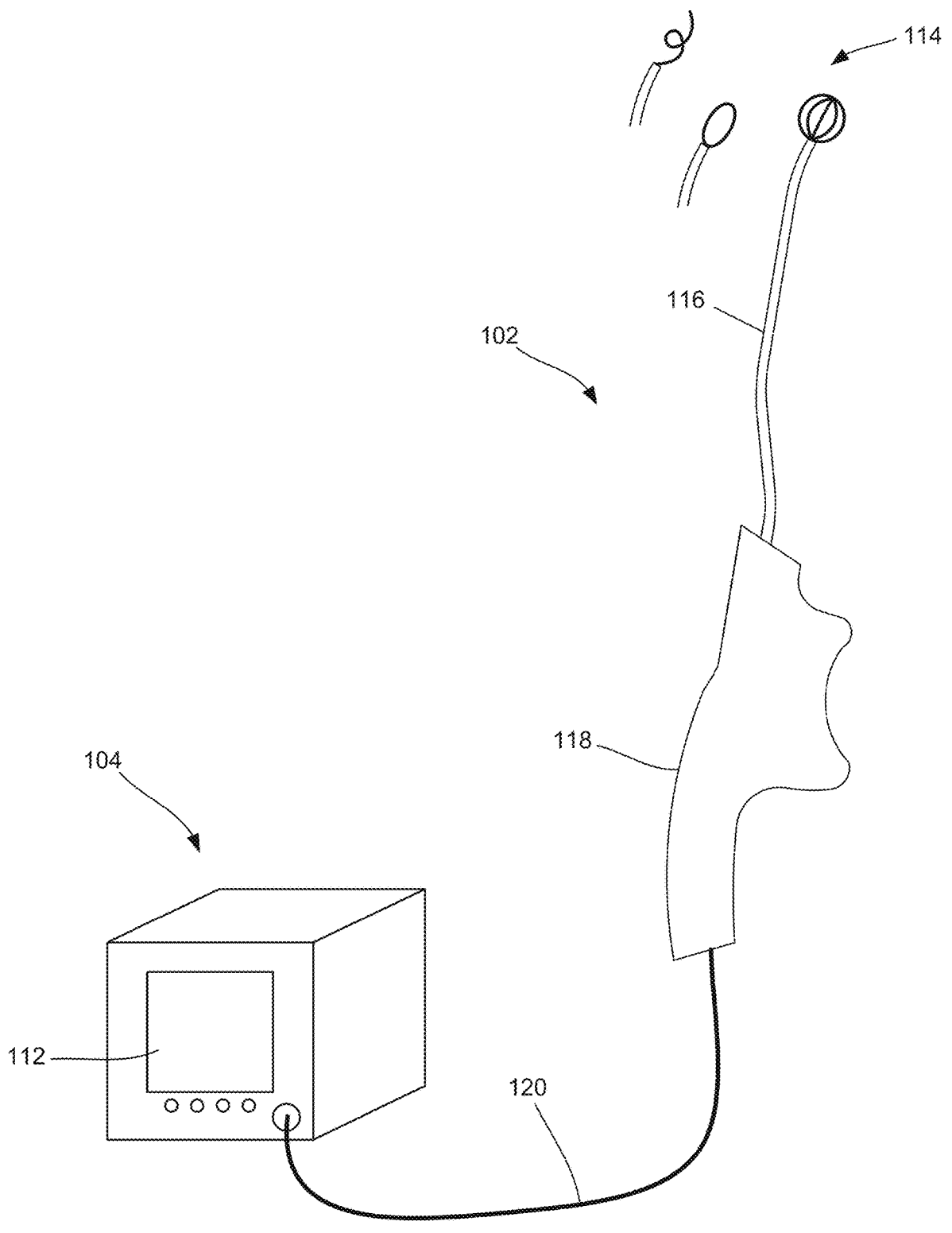
FIG. 3 is a diagrammatic illustration of the console coupled to the handheld device consistent with the present disclosure, further illustrating different embodiments of end effectors for use with the handheld device for delivering energy to tissue at one or more target sites.

FIGS. 2A and 2B are diagrammatic illustrations of a therapeutic system 100 for treating chronic sinusitis conditions of a patient using a handheld device 102 according to some embodiments of the present disclosure. The system 100 generally includes a device 102 and a console 104 to which the device 102 is to be connected. FIG. 3 is a diagrammatic illustrations of the console 104 coupled to the handheld device 102 illustrating exemplary embodiments of an end effector 114 for delivering energy to tissue at the one or more target sites of a patient for the treatment of chronic sinusitis. As illustrated, the device 102 is a handheld device, which includes end effector 114, a shaft 116 operably associated with the end effector 114, and a handle 118 operably associated with the shaft 116. The end effector 114 may be collapsible/retractable and expandable, thereby allowing for the end effector 114 to be minimally invasive (i.e., in a collapsed or retracted state) upon delivery to one or more target sites within a patient and then expanded once positioned at the target site. It should be noted that the terms "end effector" and "therapeutic assembly" may be used interchangeably throughout this disclosure.

For example, a surgeon or other medical professional performing a procedure can utilize the handle 118 to manipulate and advance the shaft 116 to a desired target site, wherein the shaft 116 is configured to locate at least a distal portion thereof intraluminally at a treatment or target site within a portion of the patient associated with tissue to undergo therapeutic stimulation for subsequent treatment of an associated condition or disorder.

In the present example, the tissue to be treated is neural tissue, specifically parasympathetic nerves that control autonomic function of the sinuses, such that electrotherapeutic stimulation thereof results in treatment of an associated neurological condition. The target site may be a region, volume, or area in which the target nerves are located and may differ in size and shape depending upon the anatomy of the patient. Once positioned, the end effector 114 may be deployed and subsequently deliver energy to the one or more target sites. The energy delivered may be non-therapeutic stimulating energy at a frequency for locating neural tissue and further sensing one or more properties of the neural tissue. For example, the end effector 114 may include an electrode array, which includes at least a subset of electrodes configured to sense the presence of neural tissue at a respective position of each of the electrodes, as well as morphology of the neural tissue, wherein such data may be used for determining, via the console 104, the type of neural tissue, depth of neural tissue, and location of neural tissue.

Based on the identification of the neural tissue type, the console 104 is configured to determine a specific treatment pattern for controlling delivery of energy from the end effector 114 upon the target site at a specific level for a specific period of time to the tissue of interest (i.e., the targeted tissue) sufficient to ensure successful ablation/modulation of the targeted tissue while minimizing and/or preventing collateral damage to surrounding or adjacent non-targeted tissue at the target site. Accordingly, the end effector 114 is able to therapeutically modulate nerves of interest, particularly nerves associated with a peripheral neurological conditional or disorder so as to treat such condition or disorder, while minimizing and/or preventing collateral damage.

For example, the end effector 114 may include at least one energy delivery element, such as an electrode, configured to delivery energy to the target tissue which may be used for sensing presence and/or specific properties of tissue (such tissue including, but not limited to, muscle, nerves, blood vessels, bones, etc.) for therapeutically modulating tissues of interest, such as neural tissue. For example, one or more electrodes may be provided by one or more portions of the end effector 114, wherein the electrodes may be configured to apply electromagnetic neuromodulation energy (e.g., radiofrequency (RF) energy) to target sites. In other embodiments, the end effector 114 may include other energy delivery elements configured to provide therapeutic neuromodulation using various other modalities, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power.

In some embodiments, the end effector 114 may include one or more sensors (not shown), such as one or more temperature sensors (e.g., thermocouples, thermistors, etc.), impedance sensors, and/or other sensors. The sensors and/or the electrodes may be connected to one or more wires extending through the shaft 116 and configured to transmit signals to and from the sensors and/or convey energy to the electrodes.

As shown, the device 102 is operatively coupled to the console 104 via a wired connection, such as cable 120. It should be noted, however, that the device 102 and console 104 may be operatively coupled to one another via a wireless connection. The console 104 is configured to provide various functions for the device 102, which may include, but is not limited to, controlling, monitoring, supplying, and/or otherwise supporting operation of the device 102. For example, when the device 102 is configured for electrode-based, heat-element-based, and/or transducer-based treatment, the console 104 may include an energy generator 106 configured to generate RF energy (e.g., monopolar, bipolar, or multi-polar RF energy), pulsed electrical energy, microwave energy, optical energy, ultrasound energy (e.g., intraluminally-delivered ultrasound and/or HIFU), direct heat energy, radiation (e.g., infrared, visible, and/or gamma radiation), and/or another suitable type of energy.

In some embodiments, the console 104 may include a controller 107 communicatively coupled to the device 102. However, in the embodiments described herein, the controller 107 may generally be carried by and provided within the handle 118 of the device 102. The controller 107 is configured to initiate, terminate, and/or adjust operation of one or more electrodes provided by the end effector 114 directly and/or via the console 104. For example, the controller 107 can be configured to execute an automated control algorithm and/or to receive control instructions from an operator (e.g., surgeon or other medical professional or clinician). For example, the controller 107 and/or other components of the console 104 (e.g., processors, memory, etc.) can include a computer-readable medium carrying instructions, which when executed by the controller 107, causes the device 102 to perform certain functions (e.g., apply energy in a specific manner, detect impedance, detect temperature, detect nerve locations or anatomical structures, etc.). A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory.

The console 104 may further be configured to provide feedback to an operator before, during, and/or after a treatment procedure via evaluation/feedback algorithms 110. For example, the evaluation/feedback algorithms 110 can be configured to provide information associated with the location of nerves at the treatment site, the temperature of the tissue at the treatment site, and/or the effect of the therapeutic neuromodulation on the nerves at the treatment site. In certain embodiments, the evaluation/feedback algorithm 110 can include features to confirm efficacy of the treatment and/or enhance the desired performance of the system 100. For example, the evaluation/feedback algorithm 110, in conjunction with the controller 107, can be configured to monitor temperature at the treatment site during therapy and automatically shut off the energy delivery when the temperature reaches a predetermined maximum (e.g., when applying RF energy) or predetermined minimum (e.g., when applying cryotherapy). In other embodiments, the evaluation/feedback algorithm 110, in conjunction with the controller 107, can be configured to automatically terminate treatment after a predetermined maximum time, a predetermined maximum impedance rise of the targeted tissue (i.e., in comparison to a baseline impedance measurement), a predetermined maximum impedance of the targeted tissue, and/or other threshold values for biomarkers associated with autonomic function. This and other information associated with the operation of the system 100 can be communicated to the operator via a graphical user interface (GUI) 112 provided via a display on the console 104 and/or a separate display (not shown) communicatively coupled to the console 104, such as a tablet or monitor, to thereby provide visual and/or audible alerts to the operator. The GUI 112 may generally provide operational instructions for the procedure, such as directing the operator to select which sino-nasal cavity to treat, indicating when the device 102 is primed and ready to perform treatment, and further providing status of therapy during the procedure, including indicating when the treatment is complete.

For example, in some embodiments, the end effector 114 and/or other portions of the system 100 can be configured to detect various parameters of the heterogeneous tissue at the target site to determine the anatomy at the target site (e.g., tissue types, tissue locations, vasculature, bone structures, foramen, sinuses, etc.), locate nerves and/or other structures, and allow for neural mapping. For example, the end effector 114 may be configured to detect impedance, dielectric properties, temperature, and/or other properties that indicate the presence of neural fibers in the target region.

As shown in FIG. 2A, the console 104 further includes a monitoring system 108 configured to receive data from the end effector 114 (i.e., detected electrical and/or thermal measurements of tissue at the target site), specifically sensed by appropriate sensors (e.g., temperature sensors and/or impedance sensors, or the like), and process this information to identify the presence of nerves, the location of nerves, neural activity at the target site, and/or other properties of the neural tissue, such a physiological properties (e.g., depth), bioelectric properties, and thermal properties. The nerve monitoring system 108 can be operably coupled to the electrodes and/or other features of the end effector 114 via signal wires (e.g., copper wires) that extend through the cable 120 and through the length of the shaft 116. In other embodiments, the end effector 114 can be communicatively coupled to the nerve monitoring system 108 using other suitable communication means.

The nerve monitoring system 108 can determine neural locations and activity before therapeutic neuromodulation to determine precise treatment regions corresponding to the positions of the desired nerves. The nerve monitoring system 108 can further be used during treatment to determine the effect of the therapeutic neuromodulation, and/or after treatment to evaluate whether the therapeutic neuromodulation treated the target nerves to a desired degree. This information can be used to make various determinations related to the nerves proximate to the target site, such as whether the target site is suitable for neuromodulation. In addition, the nerve monitoring system 108 can also compare the detected neural locations and/or activity before and after therapeutic neuromodulation, and compare the change in neural activity to a predetermined threshold to assess whether the application of therapeutic neuromodulation was effective across the treatment site.

For example, the nerve monitoring system 108 can further determine electroneurogram (ENG) signals based on recordings of electrical activity of neurons taken by the end effector 114 before and after therapeutic neuromodulation. Statistically meaningful (e.g., measurable or noticeable) decreases in the ENG signal(s) taken after neuromodulation can serve as an indicator that the nerves were sufficiently ablated. Additional features and functions of the nerve monitoring system 108, as well as other functions of the various components of the console 104, including the evaluation/feedback algorithms 110 for providing real-time feedback capabilities for ensuring optimal therapy for a given treatment is administered, are described in at least U.S. Publication No. 2016/0331459 and U.S. Publication No. 2018/0133460, the contents of each of which are incorporated by reference herein in their entireties.

The device 102 provides access to target sites within the sinuses, specifically the paranasal sinus cavities and associated ostia. Accordingly, the devices 102 provides access to neural tissue present within such locations. In particular, the ostia of the sinuses may include areas of high nerve density, including certain portions thereof which include proximal locations for efferent nerves to the associated cavity.

Figure 4:
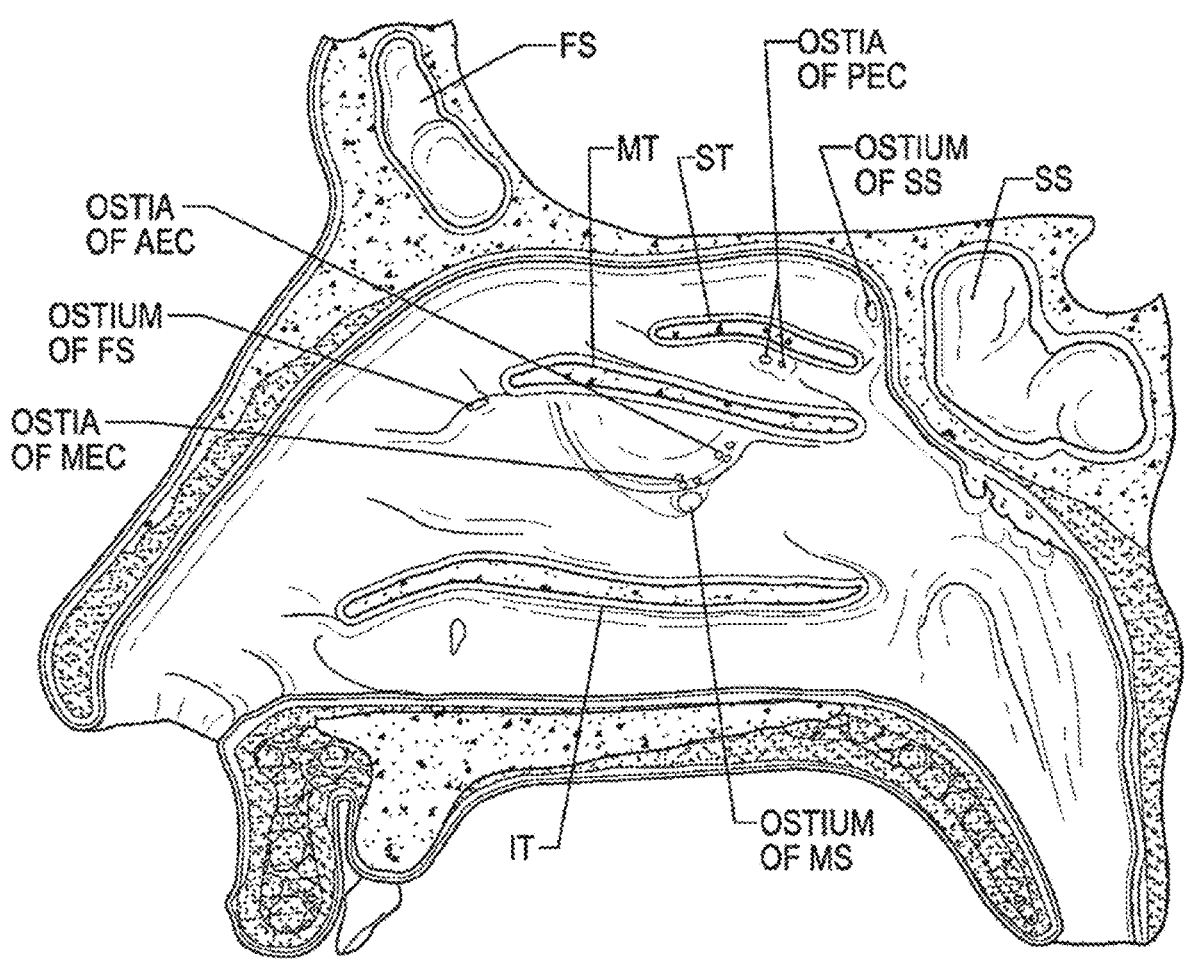
FIG. 4 is a partial cut-away side view illustrating target sites proximate to ostia of nasal sinuses for a therapeutic neuromodulation device configured in accordance with embodiments of the present invention.

FIG. 4 is a partial cut-away side view illustrating target sites proximate to ostia of nasal sinuses for a therapeutic neuromodulation device configured in accordance with embodiments of the present invention. It should be noted that any of the end effectors (and the overall system) described herein can be used to therapeutically modulate nerves that innervate the paranasal sinuses to treat chronic sinusitis and/or similar indications. As previously described, the paranasal sinuses include the frontal sinuses (FS), the sphenoidal sinuses (SS), the maxillary sinuses (MS) (not shown in FIG. 4), and the ethmoidal sinuses or ethmoidal cells (not shown in FIG. 4), which include the posterior ethmoidal cells (PEC), the middle ethmoidal cells (MEC), and the anterior ethmoidal cells (AEC). Each sinus opens to the nasal cavity at one or more discrete ostia.

FIG. 4 illustrates the general locations of the ostium of the frontal sinus, the sphenoidal sinus, the maxillary sinus, and the ostia of posterior, middle, and anterior ethmoidal cells. Parasympathetic nerves innervate the mucosa of the sinuses and stimulate the production of mucus in the sinuses. Hyperactivity of the parasympathetic nerves innervating the sinuses can cause hyper production of mucus and the soft tissue engorgement. The inflammation of the soft tissue proximate to the sinuses can cause can obstruct the conduit between a sinus and the nasal cavity and block the ostium to the sinus. In addition, the hyperactive mucosa and/or the blockage of the ostium can cause the pooling of mucosal secretions within the sinus occurs due to the lack of drainage from the sinus. This can lead to infection and, eventually, a chronic sinusitis state.

Therapeutic modulation the parasympathetic nerves that control autonomic function of the sinuses is expected to reduce or eliminate the hyperactive mucosal secretions and soft tissue engorgement and, thereby, treat chronic sinusitis or related indications.

The various embodiments of end effectors of the present invention can be used to apply therapeutically effective neuromodulation energy at or proximate to the ostia of the affected sphenoidal, maxillary, frontal, and/or ethmoidal sinuses to modulate the autonomic function of the sinuses. For example, the treatment device 102 can be used to apply RF energy, microwave energy, ultrasound energy, cryotherapeutic cooling, therapeutic heating, plasma ablation, and/or laser ablation to treatment sites at and around the ostia of the sinuses, within the sinus cavities, or a combination of both ostia and cavities. For example, the end effector 114 can be delivered intraluminally via the nasal passage and through the superior, middle, and/or inferior meatuses to access the ostium or ostia of the desired sinus. Furthermore, neural mapping techniques can be used to locate or detect the parasympathetic nerves that innervate the ostia before, during, and/or after treatment. The application of therapeutic neuromodulation at the target sites proximate to the sinus ostia can disrupt the parasympathetic signals to the sinus tissues, leading to the opening of the ostia and the ability to drain fluid, thereby treating the underlying cause of the condition.

As previously described, the treatment device 102 may include various forms of an end effector 114 shaped and/or sized to be positioned within a nasal cavity and relative to target sites associated with the sinuses, including, but not limited to, sinus cavities, including sinus cavity walls, and ostia of the sinuses, as well as a combination of both.

FIGS. 5A-5D are side views illustrating various embodiments of end effectors consistent with the present disclosure. As illustrated, the various end effectors 114a-114d may generally include one or more flexible support elements extending from, or operably coupled to, the shaft 116. Furthermore, the one or more flexible support elements may include at least one energy delivering element for delivering treatment energy to the desired target site. The flexible support elements may include a specific geometry once deployed within the nasal cavity to completement anatomy of a respective location, such that a given support element may contact and generally conform to a shape of a respective location (i.e., sinus cavity wall, surface of a sinus ostium, etc.), at which point energy may be delivered to the underlying tissue (i.e., neural tissue) at a target site.

Figures 5A, 5B, 5C, 5D:
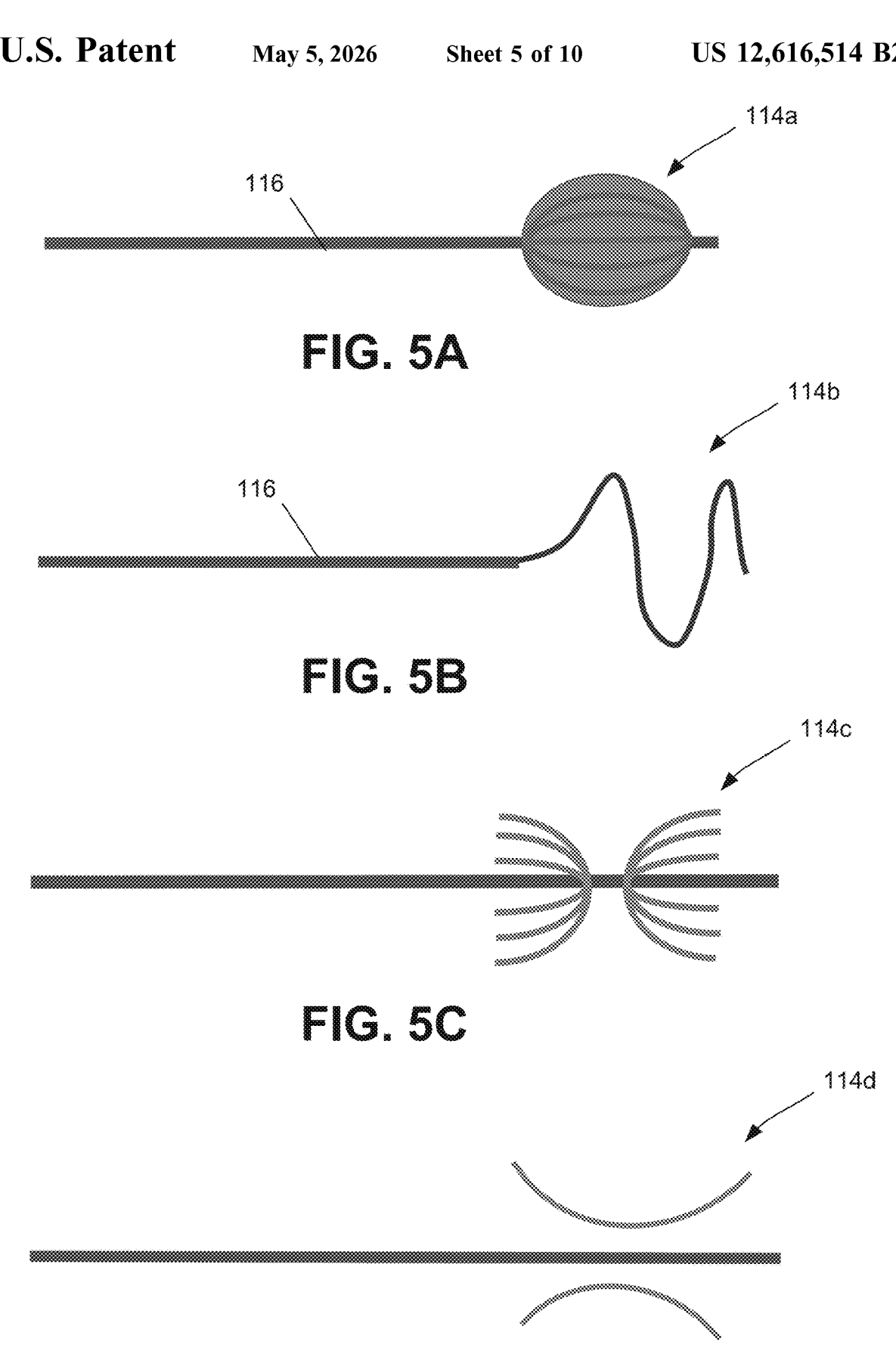
FIGS. 5A, 5B, 5C, and 5D are side views illustrating various embodiments of end effectors consistent with the present disclosure.

For example, as illustrated in FIG. 5A, one embodiment of an end effector 114 may be comprised of a plurality of connected flexible support elements that, as a whole, form an expandable frame or basket able to transition from a retracted state (i.e., smaller radial profile) to a deployed state (i.e., expanded to a larger radial profile). In the illustrated embodiment, the end effector 114a may further include an inflatable member (e.g., balloon or the like) provided within the frame or basket of flexible support elements.

In other embodiments, the end effector may include one or more flexible support elements having a helical- or coil-type shape once deployed, as shown in FIG. 5B regarding end effector 114b.

Yet still, on other embodiments, the end effector may include a dogbone- or dumbbell-type configuration, as shown in FIG. 5C with regards to end effector 114c. As shown, a first set of flexible support elements forms a first segment and a second set of flexible support elements forms an opposing second segment. In this embodiment, the first and second segments generally oppose one another in that the first and second segments extend in opposing directions along a longitudinal axis of the shaft 116. The first segment and second segments each have an open-ended circumferential shape when in the deployed state. As shown, the open-ended circumferential shape generally resembles a blooming flower. As shown in FIG. 5D, the end effector 114d may include a first flexible support element and a second flexible support element provided on opposing sides of the shaft 116, wherein each of the first and second flexible support elements are arched away from one another.

It should be noted that the end effector 114 may also include one or more inflatable members (i.e., balloons or the like), either alone or incorporated with the flexible support element(s).

It should be noted that the various characteristics, features, and functions of the end effectors described herein, as well as additional end effector embodiments or therapeutic assemblies are described in at least U.S. Publication No. 2016/0331459, U.S. Publication No. 2018/0133460, U.S. Publication No. 2020/0179682, and U.S. Publication No. 2020/0405383, the contents of each of which are incorporated by reference herein in their entireties. Furthermore, deployment of the end effectors and subsequent control over the delivery of energy from the end effectors with the device 102 and system 100 described herein are further described in at least U.S. Publication No. 2016/0331459, U.S. Publication No. 2018/0133460, U.S. Publication No. 2020/0179682, and U.S. Publication No. 2020/0405383, the contents of each of which are incorporated by reference herein in their entireties.

The flexible support elements of the end effectors described herein may include one or more energy delivering elements associated therewith. The energy delivering elements may include electrodes or the like configured to apply electromagnetic neuromodulation energy (e.g., radiofrequency (RF) energy) to target sites. It should be noted that, in other embodiments, the end effector may include other energy delivery elements configured to provide therapeutic neuromodulation using various other modalities, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power.

Figure 6:
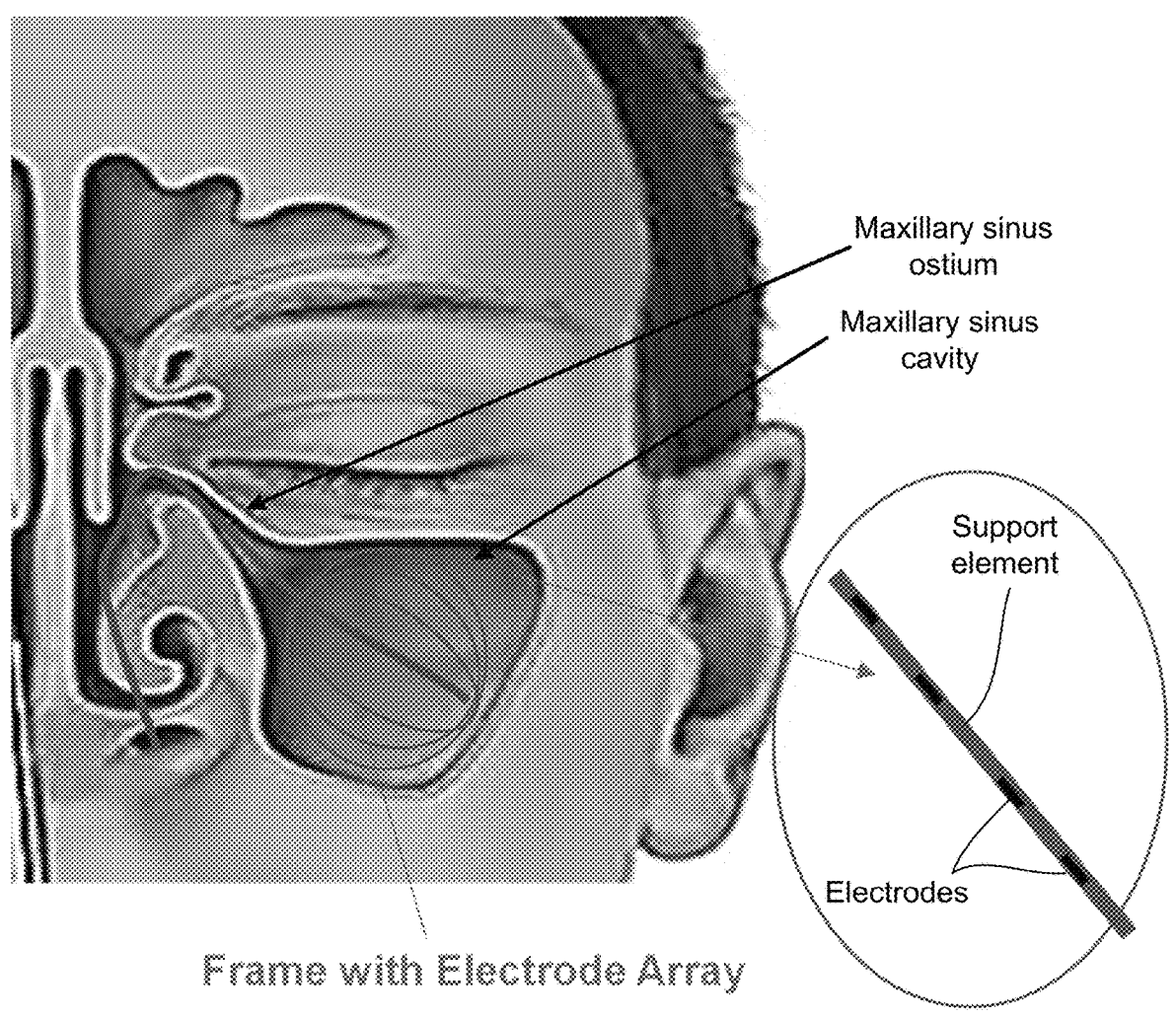
FIG. 6 illustrates deployment of one embodiment of an expandable end effector of the present invention within the maxillary sinus cavity for placement of energy delivery elements into contact with the cavity walls at desired target sites.

FIG. 6 illustrates deployment of one embodiment of an expandable end effector 114a within the maxillary sinus cavity for placement of energy delivery elements (i.e., electrodes) into contact with the walls within the maxillary sinus cavity.

Figure 7:
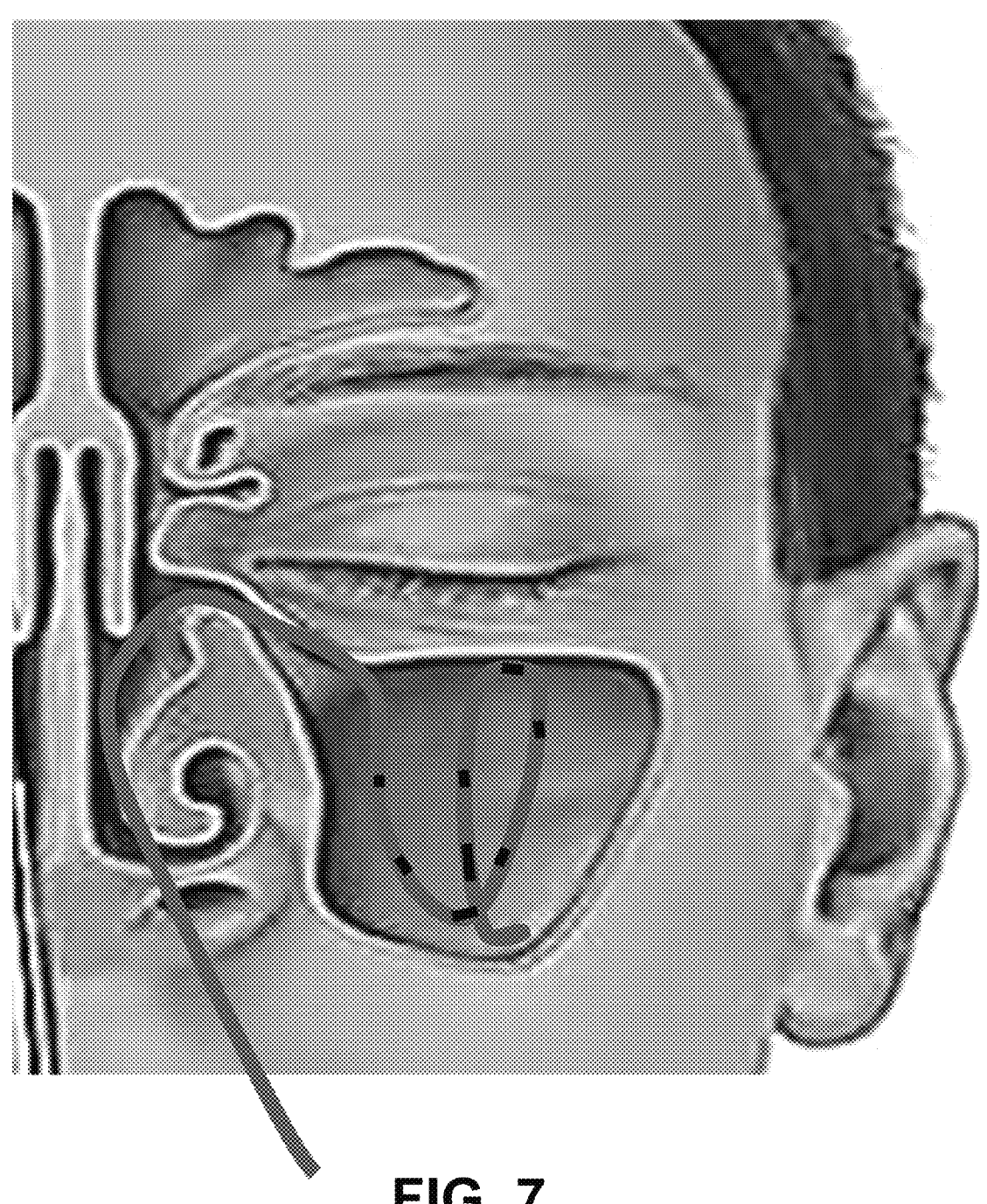
FIG. 7 illustrates deployment of another embodiment of an end effector within the maxillary sinus cavity for placement of energy delivery elements into contact with the cavity walls at desired target sites.

FIG. 7 similarly illustrates deployment of end effector 114b within the maxillary sinus cavity for placement of energy delivery elements into contact with the cavity walls at desired target sites.

Figure 8:
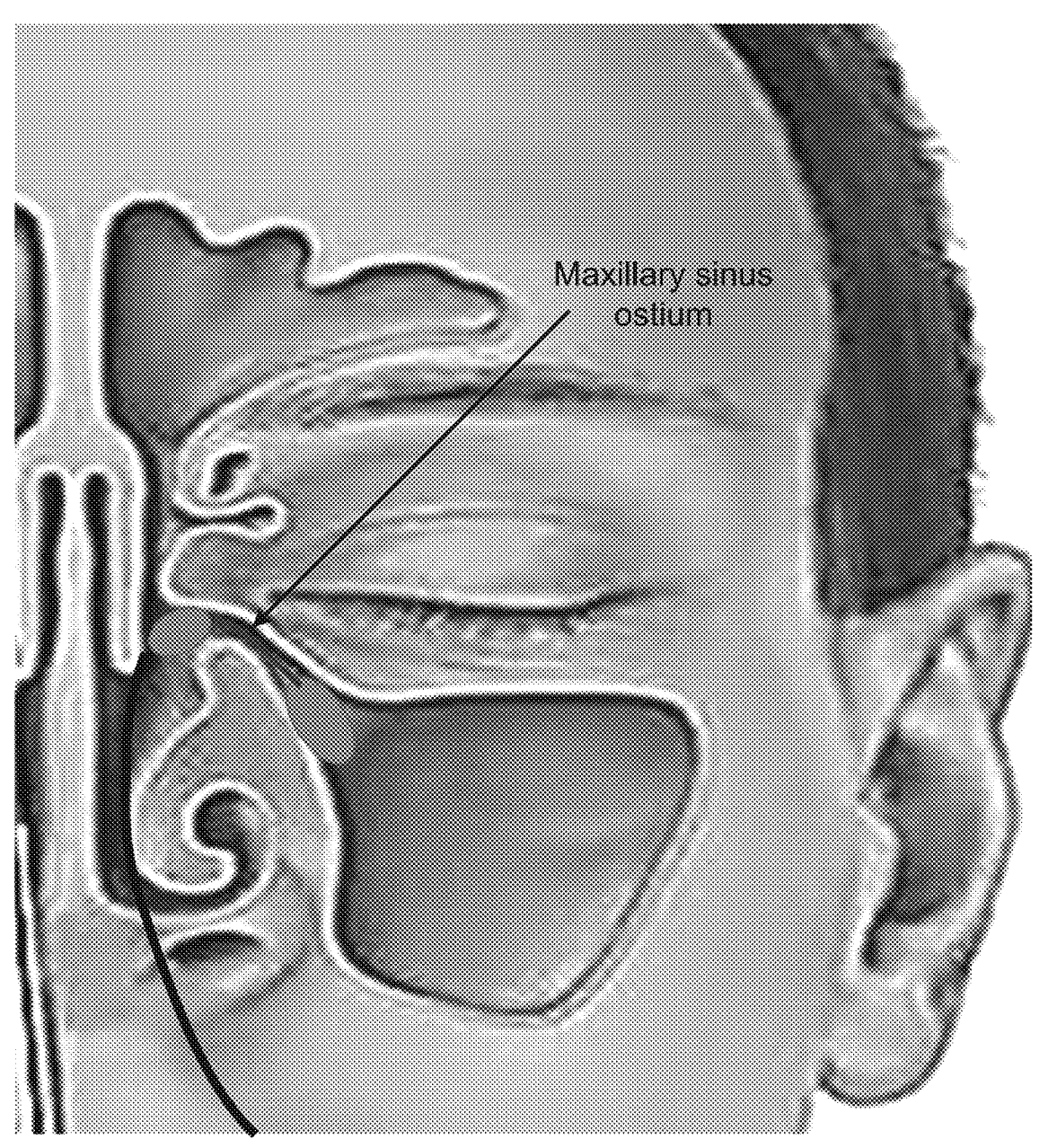
FIG. 8 illustrates deployment of another embodiment of an end effector within the maxillary sinus ostium for placement of energy delivery elements into contact with ostium walls at desired target sites.
Figure 9:
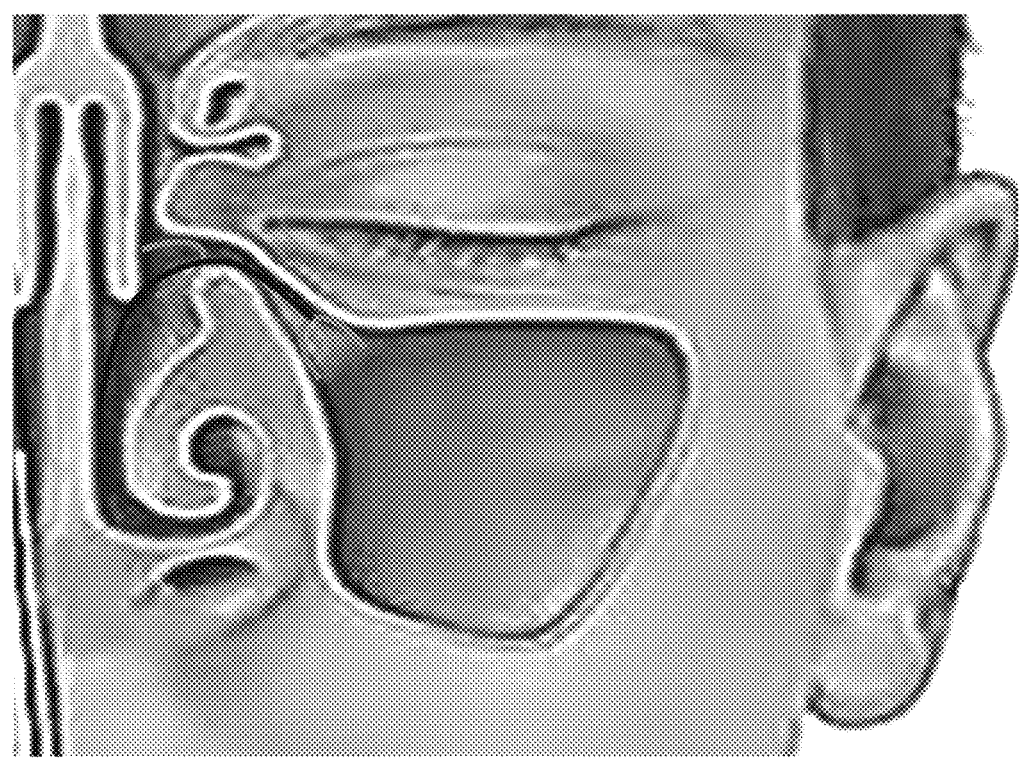
FIG. 9 illustrates deployment of another embodiment of an end effector within the maxillary sinus ostium for placement of energy delivery elements into contact with ostium walls at desired target sites.
Figure 10:
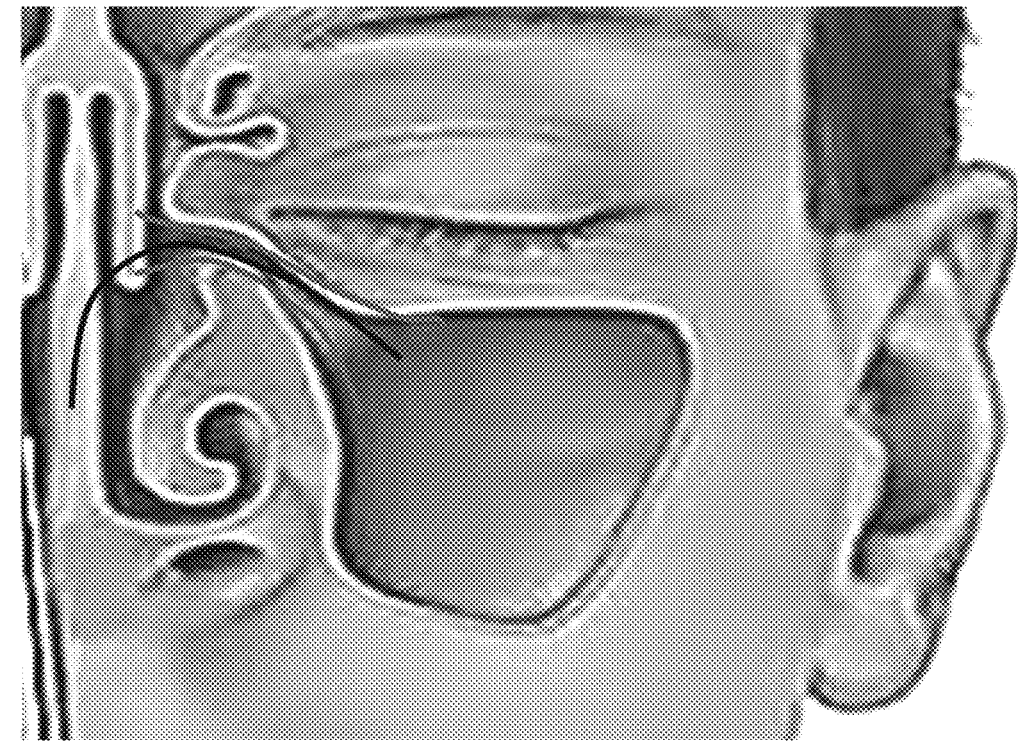
FIG. 10 illustrates deployment of another embodiment of an end effector within the maxillary sinus ostium for placement of energy delivery elements into contact with ostium walls at desired target sites.

FIGS. 8, 9, and 10 illustrates deployment of other embodiments of end effectors within the maxillary sinus ostium for placement of energy delivery elements into contact with ostium walls at desired target sites. For example, FIG. 8 illustrates an end effector consisting of two inflatable members separated from one another and configured to contact proximal and distal portions of the ostium, respectively. FIG. 9 illustrates deployment of end effector 114c within the maxillary sinus ostium, in which the first segment is positioned at a proximal portion of the ostium and the second segment is positioned at a distal portion of the ostium. FIG. 10 illustrates deployment of end effector 114d within the maxillary sinus ostium, in which the first and second flexible support elements (disposed on opposing sides of the shaft) are positioned along opposing walls of the ostium.

As illustrated in FIGS. 6-10, once the end effector is delivered within the sino-nasal cavity and positioned relative to the desired target site(s) (i.e., ostia and/or cavities of the sinuses), portions of the end effector (i.e., flexible support elements, outer surface of inflatable body, etc.) can transition to a deployed state, having a specific shape and/or size corresponding to anatomical structures within the sino-nasal cavity and associated with target sites to undergo delivery of therapeutic energy for treatment of chronic sinusitis. As such, once deployed, the energy delivery element(s) can be positioned at desired locations for focused application of energy to the underlying targeted neural tissue at the one or more target sites.

As previously described, parasympathetic nerves innervate the mucosa of the sinuses and stimulate the production of mucus in the sinuses. Hyperactivity of the parasympathetic nerves innervating the sinuses can cause hyper production of mucus and the soft tissue engorgement. The inflammation of the soft tissue proximate to the sinuses can cause can obstruct the conduit between a sinus and the nasal cavity and block the ostium to the sinus. In addition, the hyperactive mucosa and/or the blockage of the ostium can cause the pooling of mucosal secretions within the sinus occurs due to the lack of drainage from the sinus. This can lead to infection and, eventually, a chronic sinusitis state.

Therapeutic modulation the parasympathetic nerves that control autonomic function of the sinuses is expected to reduce or eliminate the hyperactive mucosal secretions and soft tissue engorgement and, thereby, treat chronic sinusitis or related indications.

The end effectors of the present invention can be used to apply therapeutically effective neuromodulation energy at or proximate to the ostia of the affected sphenoidal, maxillary, frontal, and/or ethmoidal sinuses to modulate the autonomic function of the sinuses. For example, the treatment device 102 can be used to apply RF energy, microwave energy, ultrasound energy, cryotherapeutic cooling, therapeutic heating, plasma ablation, and/or laser ablation to treatment sites at and around the ostia of the sinuses, within the sinus cavities, or a combination of both ostia and cavities. The application of therapeutic neuromodulation at the target sites proximate to the sinus ostia can disrupt the parasympathetic signals to the sinus tissues, leading to the opening of the ostia and the ability to drain fluid, thereby treating the underlying cause of the condition.

It should be noted that, in addition or alternatively to the use of the end effectors described herein, systems and methods of the present invention may further include the use of implants within the ostia and/or cavities of the paranasal sinuses. The implants may serve as a means of mechanical support, targeted drug delivery, and/or placement of energy delivery elements into direct contact with target sites associated with the paranasal sinuses.

Figure 11:
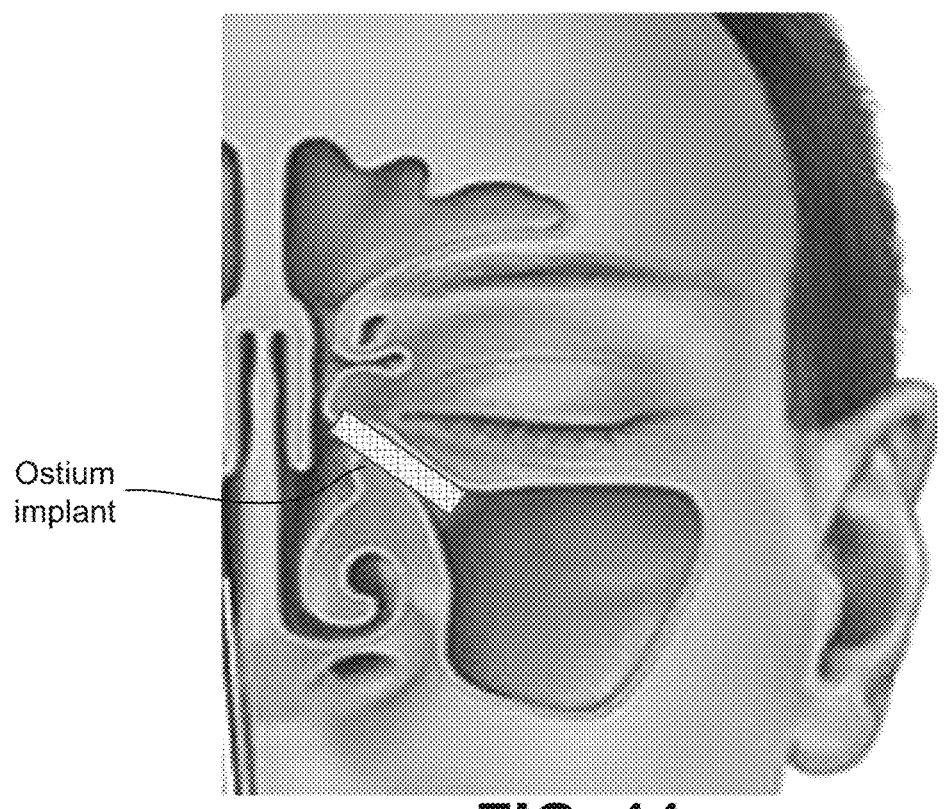
FIG. 11 illustrates deployment of an implant of the present invention within the maxillary sinus ostium to serve as mechanical support of the ostium, provide targeted drug delivery, and/or provide placement of energy delivery elements into contact with ostium walls at desired target sites.

FIG. 11 illustrates deployment of an implant of the present invention within the maxillary sinus ostium to serve as mechanical support of the ostium, provide targeted drug delivery, and/or provide placement of energy delivery elements into contact with ostium walls at desired target sites.

Figure 12:
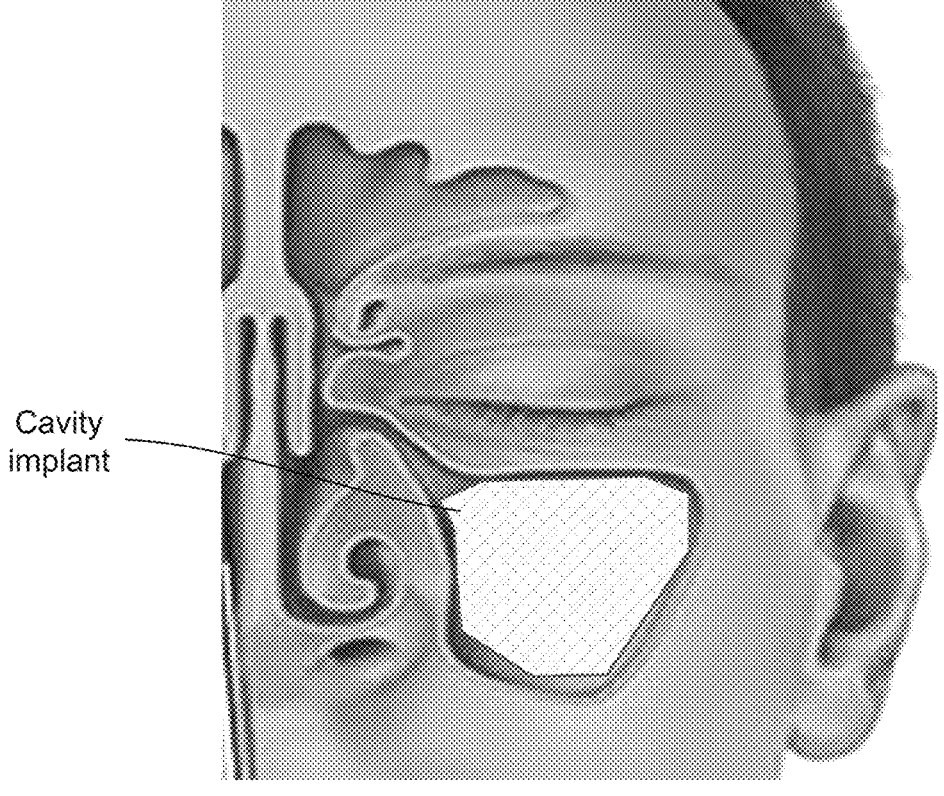
FIG. 12 illustrates deployment of an implant of the present invention within the maxillary sinus cavity to serve as mechanical support of the sinus, provide targeted drug delivery, and/or provide placement of energy delivery elements into contact with cavity walls at desired target sites.

FIG. 12 illustrates deployment of an implant of the present invention within the maxillary sinus cavity to serve as mechanical support of the sinus, provide targeted drug delivery, and/or provide placement of energy delivery elements into contact with cavity walls at desired target sites.

The implants may include bioabsorbable material, such that, after a period of time, the material naturally breaks down and is absorbed. In other embodiments, the implant may not be bioabsorbable and thus will require removal after a period of time (i.e., 1 week, 1 month, 6 months, etc.).

For targeted drug delivery, the implant may be coated with, or otherwise contain, a slow-release medicament, which, when in contact with the cavity or ostium walls, the implant will slowly release the medicament to the targeted tissue.

In some embodiments, the implant may further provide neuromodulation capabilities. For example, the implant may include energy delivering elements, such as electrodes or the like, which may be coupled to the device 102 via a wired or wireless connection.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A method for treating chronic sinusitis, the method comprising:

advancing an end effector, disposed at a distal end of a shaft of a treatment device, within a sino-nasal cavity of a patient;

positioning and deploying the end effector relative to one or more target sites associated with at least one of an ostium and cavity of a paranasal sinus, wherein the end effector comprises a first segment comprising a first set of flexible support elements and a second segment comprising a second set of flexible support elements, wherein the first and second segments each have an open-ended circumferential shape when deployed and generally oppose one another in that the first and second segments extend in opposing directions along a longitudinal axis of the shaft; and delivering energy, from a plurality of energy delivery elements provided on the first and second segments, at the one more target to disrupt neural signals to mucus producing and/or mucosal engorgement elements associated with the paranasal sinus.

2. The method of claim 1, wherein the paranasal sinus is selected from the group consisting of a frontal sinus, a sphenoidal sinus, a maxillary sinus, and an ethmoidal sinus.

3. The method of claim 1, wherein delivering energy results in ablation of targeted tissue at multiple locations to thereby disrupt the multiple neural signals to the mucus producing and/or mucosal engorgement elements.

4. The method of claim 3, wherein the ablation is thermal ablation.

5. The method of claim 3, wherein the ablation is caused by delivery of radio-frequency energy.

6. The method of claim 3, further comprising receiving feedback, prior to, during, and/or after the ablation.

7. The method of claim 1, wherein each of the flexible support elements includes one or more energy delivery elements provided thereon.

8. The method of claim 7, wherein each of the flexible support elements comprises a plurality of energy delivery elements provided thereon.

9. The method of claim 7, wherein the end effector is transformable from a retracted configuration to an expanded configuration.

10. The method of claim 9, wherein the one or more flexible support elements comprises shape memory material.

11. The method of claim 9, wherein, when in the expanded configuration, the end effector positions the one or more energy delivery elements relative to parasympathetic nerves inverting the paranasal sinus.

12. The method of claim 11, wherein the disrupting of neural signals reduces hyperactive mucosal secretions and soft tissue engorgement of the paranasal sinus.

13. The method of claim 1, wherein the end effector comprises at least one inflatable member.

\* \* \* \* \*